United States Patent [19]
Leu

[11] Patent Number: 6,013,610
[45] Date of Patent: Jan. 11, 2000

[54] SOLID COMPOSITION FOR FORMING ARTIFICIAL HOT SPRINGS

[76] Inventor: Shiow Jiuan Freida Leu, No. 487, Noan Noan St., Noan Noan District, Keelung City, Taiwan

[21] Appl. No.: 09/188,527

[22] Filed: Nov. 10, 1998

[51] Int. Cl.⁷ ..................................................... A61K 7/50
[52] U.S. Cl. ........................ 510/141; 510/130; 510/151; 424/44; 424/401; 424/466
[58] Field of Search .................................. 510/130, 135, 510/141, 151; 424/44, 466, 401

[56] References Cited

U.S. PATENT DOCUMENTS

| | | | |
|---|---|---|---|
| 4,879,105 | 11/1989 | Yorozu | 424/44 |
| 5,106,623 | 4/1992 | Mori et al. | 424/195.1 |
| 5,286,755 | 2/1994 | Kauffmann et al. | 514/944 |
| 5,380,753 | 1/1995 | Yoshida et al. | 514/474 |
| 5,626,854 | 5/1997 | Ichii et al. | 424/401 |

Primary Examiner—Necholus Ogden
Attorney, Agent, or Firm—Bacon & Thomas

[57] ABSTRACT

A solid state bath agent containing Na2CO3 (Sodium Carbonate), NaHCO3 (Sodium Bicarbonate), Na2SO4 (Sodium Sulfate), Citric acid, CMC (Carboxymethyl Cellulose), Bactericide, Silicone oil, Vitamin E, Vitamin C, AHA and fragrance. Na2CO3, NaHCO3, Na2SO4 and Citric acid are dried by hot air, then mixed with the other materials and then pressed into individual bath cakes (bath balls), and then the finished individual bath cakes (bath balls) are well packed in an air-tight sealing container.

4 Claims, No Drawings

SOLID COMPOSITION FOR FORMING ARTIFICIAL HOT SPRINGS

BACKGROUND OF THE INVENTION (a) Field of the Invention

The present invention relates to a solid state bath agent made of high molecular polymers and inorganic substance that can be quickly dissolved in water, forming an artificial hotspring.

(b) Description of the Prior Art

Natural hotspring may cure skin and limb joint diseases because it contains chemical substance and gases helpful to the health. For example, natural hotspring contains CO2, that can be used to heal nervous diseases, women's diseases as well as heart and blood vessel diseases. However, it is difficult to most people to take a hotspring bath regularly.

SUMMARY OF THE INVENTION

It is the main object of the present invention to provide a solid state bath agent which is made by mixing high molecular polymers and inorganic substance into a mixture and then pressing the mixture into solid pieces of finished product containing Na2CO3, NaHCO3 and Na2SO4. When the solid state bath agent is put in water, it is immediately dissolved, forming an artificial hotspring, that stimulates the circulation of blood of the person who bathes in it. It is another object of the present invention to provide a solid state bath agent that can be added with contains skin-care softener and nutrient, and bactericide during its production.

DETAILED DESCRIPTION OF THE PREFERRED EMBODIMENT

A solid state bath agent in accordance with the present invention contains Na2CO3(Sodium Carbonate), NaHCO3 (Sodium Bicarbonate), Na2SO4(Sodium Sulfate), Citric acid, CMC (Carboxymethyl Cellulose), Bactericide, Silicone oil, Vitamin E, Vitamin C, alpha-aliphatic-hydroxylic acids (AHA) and fragrance at the ratio by weight of:

|            |       |
|------------|-------|
| Na2CO3     | 10%   |
| NaHCO3     | 40%   |
| Na2SO4     | 14%   |
| Citric acid| 30%   |
| CMC        | 2%    |
| Bactericide| 0.1%  |
| Silicone oil| 2%   |
| Vitamin E  | 0.2%  |
| Vitamin C  | 0.5%  |
| AHA        | 1%    |
| Fragrance  | 0.2%  |

Na2CO3(Sodium Carbonate), NaHCO3(Sodium Bicarbonate), Na2SO4(Sodium Sulfate) and Citric acid are well dried, then mixed with CMC (Carboxymethyl Cellulose), Bactericide, Silicone oil, Vitamin E, Vitamin C, AHA and fragrance into a mixture. This mixture thus obtained is then molded into bath cakes (bath balls) by a molding press. The finished bath cakes (bath balls) are then packed in an air-tight sealing container.

When a bath cake (bath ball) is put in water, it is quickly dissolved in water, causing a big amount of carbon dioxide to be released in water. Because carbon dioxide can easily be dissolved in water, a high concentration of carbon dioxide is contained in water. Further, when carbon dioxide is produced and dissolved in water, ions of Na+, HCO3−, SO $4^{2-}$ and AHA, Citric Acid, Bactericide, Vitamin E, Vitamin C and Silicone oil are distributed in water to make a health protective effect to the person who bathes in it. When bathing, the temperature of the water can be heated to the desired level, or maintained in a cold condition.

The finished solid state bath agent can have any of a variety of shapes, for example, it can have a circular shape, an oval shape, a square shape, or a flake-like shape. The finished bath cakes (bath balls) individually weight within 50 g~200 g.

The ratio of the contents of the solid state bath agent may be adjusted within the limit of:

|              |           |
|--------------|-----------|
| Na2CO3       | 5~30%     |
| NaHCO3       | 15~50%    |
| Na2SO4       | 5~30%     |
| Citric acid  | 10~40%    |
| CMC          | 1~4%      |
| Bactericide  | 0.1~0.6%  |
| Silicone oil | 1~4%      |
| Vitamin E    | 0.2~1%    |
| Vitamin C    | 0.5~2%    |
| AHA          | 0.5~2%    |
| Fragrance    | 0.1~0.24% |

During the fabrication of the solid state bath agent, Na2CO3(Sodium Carbonate), NaHCO3(Sodium Bicarbonate) and Na2SO4(Sodium Sulfate) and dried by hot air at 105° C., and Citric acid is dried by hot air at 45° C. Individually packed finished product must be water-tightly sealed because an air leakage of the packing container may cause the packed finished product to release carbon dioxide. The substance of CMC is a plasticizer that imparts flexibility, workability.

What the invention claimed is:

1. A solid bath composition comprising by weight, 5 to about 30% sodium carbonate, 15 to about 50% sodium bicarbonate, 5 to about 30% sodium sulfate, 10 to about 45% citric acid, 1 to about 4% carboxymethyl cellulose, 0.01 to about 0.6% bactericide, 1 to about 4% silicone oil, 0.2 to about 1% vitamin E, 0.5 to about 2% vitamin C, 05 to about 2% alpha-aliphatic-hydroxylic acid, and 0.1 to about 0.24% fragrance.

2. The bath composition according to claim 1 comprising by weight, 10% sodium carbonate, 40% sodium bicarbonate, 14% sodium sulfate, 30% citric acid, 2% carboxymethyl cellulose, 0.1% bactericide, 2% silicone oil, 0.2% vitamin E, 0.5% vitamin C, 1% alpha-aliphatic-hydroxylic acid and 0.2% fragrance.

3. The solid bath composition of claim 1 wherein sodium carbonate, sodium bicarbonate, sodium sulfate and citric acid are dried by hot air, then mixed with the other materials and then pressed into individual pieces of finished product which are then packed in a container which is sealed air-tight.

4. The bath composition of claim 3 wherein said individual pieces of finished product each weigh within 50 g to about 200 g.

* * * * *